United States Patent [19]

Desbois

[11] 4,453,012

[45] Jun. 5, 1984

[54] PROCESS FOR THE PREPARATION OF PHENYL KETONES

[75] Inventor: Michel Desbois, Rillieux, France

[73] Assignee: Rhone-Poulenc Specialites Chimiques, Courbevoie, France

[21] Appl. No.: 393,056

[22] Filed: Jun. 28, 1982

[30] Foreign Application Priority Data

Apr. 22, 1982 [FR] France ................................ 82 6904

[51] Int. Cl.$^3$ ............................................. C07C 45/43
[52] U.S. Cl. ...................................... 568/323; 568/319; 568/322; 568/306; 260/465 D; 562/460; 564/329
[58] Field of Search ............... 568/319, 323, 322, 306, 568/404, 407; 562/460; 570/194; 260/465 D; 564/329

[56] References Cited

U.S. PATENT DOCUMENTS

| | | | |
|---|---|---|---|
| T970,006 | 5/1978 | Rose | 260/591 |
| 2,273,922 | 2/1942 | Benning et al. | 570/194 |
| 2,275,312 | 3/1942 | Tinker et al. | 570/194 |
| 2,322,562 | 3/1945 | Emerson | 568/323 |
| 2,735,868 | 2/1956 | Frevel et al. | 568/323 |
| 2,974,172 | 3/1961 | Luvisi | 260/592 |
| 3,187,057 | 6/1965 | Peter et al. | |
| 3,387,035 | 6/1968 | Gray et al. | 260/591 |
| 3,732,307 | 5/1973 | Middleton | 260/566 B |
| 3,883,594 | 5/1975 | Schmerling | 260/592 |
| 3,953,400 | 4/1976 | Dahl | 260/47 |
| 3,967,949 | 7/1976 | Benefiel et al. | 71/76 |
| 4,178,460 | 12/1979 | Berkelhammer et al. | 562/426 |
| 4,207,266 | 6/1980 | Opie | 260/651 F |
| 4,276,226 | 6/1981 | Clement et al. | 260/410,5 |

FOREIGN PATENT DOCUMENTS

| | | |
|---|---|---|
| 43861 | 1/1982 | European Pat. Off. . |
| 876690 | 5/1953 | Fed. Rep. of Germany . |
| 1645153 | 10/1970 | Fed. Rep. of Germany . |
| 2451037 | 4/1976 | Fed. Rep. of Germany . |
| 1567806 | 4/1969 | France . |
| 7721091 | 7/1977 | France . |
| 54-135756 | 10/1979 | Japan . |
| 1164817 | 9/1969 | United Kingdom . |
| 2030158 | 4/1980 | United Kingdom . |
| 2045760 | 11/1980 | United Kingdom . |

OTHER PUBLICATIONS

Buu–Hoi et al., *J. Org. Chem.*, vol. 26, pp. 2401–2402, (1961).
L. Yagupol'skii et al., *Chem. Abstracts*, 61:8217, (1964).
V. Boiko et al., *Chem. Abstracts*, 87:134226h, (1977).

*Primary Examiner*—James H. Reamer

[57] ABSTRACT

A process for the preparation of phenyl ketones, characterized in that, in a first stage, a halo- or trihalomethylbenzene is reacted with a trihalomethylated aliphatic or aromatic compound in the presence of boron trifluoride in an amount such that the absolute pressure of boron trifluoride within the reaction vessel exceeds 1 bar, and in the presence of hydrofluoric acid as a solvent, and in that, in a second stage, the resultant product is hydrolyzed. The products are used as intermediates in the synthesis of compounds having a pharmaceutical or phytosanitary (e.g., herbicidal) activity.

8 Claims, No Drawings

PROCESS FOR THE PREPARATION OF PHENYL KETONES

The instant invention is directed to a process for the preparation of phenyl ketones from halo- or trihalomethylbenzenes and trihalomethylated aliphatic or aromatic compounds.

Processes for the preparation of phenyl ketones are already known in the art. For example, in *Friedel-Crafts and Related Reactions* III, Part II, Interscience Publishers (1964), G. Olah describes the reaction of a trihalomethylated aliphatic or aromatic derivative with a halo- or trihalomethylbenzene in the presence of catalysts such as $AlCl_3$, $AlBr_3$, $FeCl_3$ and $SbCl_5$ in an organic solvent medium; in this process, the substrate can also be the solvent. The resultant product is then hydrolyzed to obtain the desired ketone.

These processes have drawbacks which can be attributed above all to the nature of the catalyst. It is necessary to use a substantial quantity of catalyst, because the catalyst forms a complex with the trihalomethyl group of the aromatic or aliphatic compound and with the product resulting from the first stage. The large quantity of, e.g., $AlCl_3$ employed requires a correspondingly large amount of water for its elimination. Moreover, its recovery on an industrial scale is impossible.

A process has now been developed which palliates the drawbacks of the prior art processes.

This invention is directed to a process for the preparation of phenyl ketones characterized in that, in a first stage, a halo- or trihalomethylbenzene is reacted with a trihalomethylated aliphatic or aromatic compound in the presence of boron trifluoride in an amount such that the absolute pressure of boron trifluoride within the reaction vessel exceeds 1 bar, and in the presence of hydrofluoric acid as a solvent, and in that, in a second stage, the resultant product is hydrolyzed.

For purposes of this invention, the terms halobenzene or trihalomethylbenzene refer both to these compounds themselves and to their analogues with one or more substituents on the benzene nucleus.

More particularly, the invention is directed to the reaction of compounds of the formula:

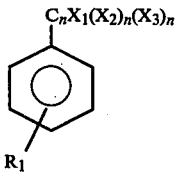

$$C_nX_1(X_2)_n(X_3)_n \quad (I)$$

wherein n is 0 or 1; $X_1$, $X_2$ and $X_3$ are identical or different and represent chlorine, bromine, iodine or fluorine; and $R_1$ represents at least one element or moiety selected from hydrogen, OH, Cl, Br, I, F, alkyl and alkoxy radicals having from 1 to 6 carbon atoms, and phenyl and phenoxy radicals substituted by at least one group more deactivating than the $C_nX_1(X_2)_n(X_3)_n$ group.

The phenyl and phenoxy radicals $R_1$ must be substituted by groups that are more deactivating than the $C_nX_1(X_2)_n(X_3)_n$ group so that the acylation reaction takes place on the benzene nucleus carrying the $C_nX_1(X_2)_n(X_3)_n$ group. Otherwise, the acylation reaction would take place on the phenyl or phenoxy radical. Examples of groups that are more deactivating than the $C_nX_1(X_2)_n(X_3)_n$ group include $NO_2$, COOH, CN and keto groups.

When $n=1$, compounds of the formula I in which $X_1$, $X_2$ and $X_3$ are identical are preferred. Among the latter, those compounds in which $X_1$, $X_2$ and $X_3$ represent fluorine are particularly preferred.

The following are examples of compounds of the formula I: chlorobenzene; fluorobenzene; bromobenzene; iodobenzene; trifluoromethylbenzene; difluorobromomethylbenzene; trichloromethylbenzene; dichlorofluoromethylbenzene; tribromomethylbenzene; dibromofluoromethylbenzene; triodomethylbenzene; o-, m- and p-fluorotoluene; o-, m- and p-dichlorobenzene; o-, m- and p-fluorophenol; o-, m- and p-fluorochlorobenzene; o-, m- and p-fluoroanisole; o-, m- and p-difluorobenzene; o-, m- and p-chlorotoluene; o-, m- and p-chloroanisole; 4-trifluoromethyl-4'-chlorobiphenyl; and 4-trifluoromethyl-2,4'-dichlorodiphenyl oxide.

Within the scope of the instant invention, the terms trihalomethylated aliphatic or aromatic compound refer to a compound of the formula:

$$R_2CX_4X_5X_6 \quad (II)$$

wherein $R_2$ represents an aliphatic or aromatic radical and $X_4$, $X_5$, and $X_6$ are identical or different and represent Br, Cl, or F.

Particularly well suited for use according to the invention are compounds of the Formula II in which $R_2$ represents an alkyl, phenyl, alkylphenyl or phenylalkyl radical or a phenyl radical bearing at least one substituent, such as, for example, halogen, $NO_2$, CN, $NH_2$ or COOH.

Examples of such compounds of Formula II include 1,1,1-trichloroethane, trichloromethylbenzene, trifluoromethylbenzene, parafluorotrichloromethylbenzene, parachlorotrifluoromethylbenzene, parachlorotrichloromethylbenzene, orthochlorotrichlormethylbenzene, metanitrotrichloromethylbenzene and 3,4-dichlorotrichloromethylbenzene.

The first stage of the process according to the invention is preferably carried out by using a quantity of hydrofluoric acid such that the molar ratio of hydrofluoric acid to the halo- or trihalomethylbenzene is between 5 and 50. Even more preferably, this ratio is between 10 and 30.

The hydrofluoric acid utilized is preferably anhydrous. The use of aqueous hydrofluoric acid would result in a useless consumption of boron trifluoride in the form of a complex of HF, $BF_3$ and $H_2O$ ($H_3O^+BF_4^-$).

The halo- or trihalomethylbenzene and the compound of Formula II are used in substantially equimolar amounts. An excess of the compound of Formula II may, however, be desirable in order to minimize the formation of polycondensation compounds.

It is particularly preferred to use a quantity of boron trifluoride such that the initial absolute pressure of $BF_3$ in the reaction vessel is between 6 and 20 bars. A pressure in excess of 20 bars is not excluded from the scope of the invention but does not offer any particular advantage. The more the pressure is increased, the higher the reaction velocity. The pressure will therefore be adjusted to maximize the efficiency of the process. If a trichloromethylated compound of Formula I or II is employed, an increase in pressure attributable to Cl-F exchange is observed.

The first stage of the process of the invention is preferably carried out at a temperature between $-20°$ C.

and 150° C. The reaction times are generally between a few minutes and several hours. The second stage is a hydrolysis that can be performed in an acid or basic medium as is conventional in the art.

A practical method for carrying out the process according to the invention is to effect the hydrolysis on the raw mixture or a mixture partially freed from HF solvent generated in the first stage. The reaction will be carried out in the presence of HF and, therefore, in an acid medium. Complete elimination of HF prior to the second stage makes it possible to operate in either a basic or acid medium. The hydrolysis is preferably carried out at a temperature between 0° C. and 80° C.

The process according to the invention can be schematically illustrated as follows:

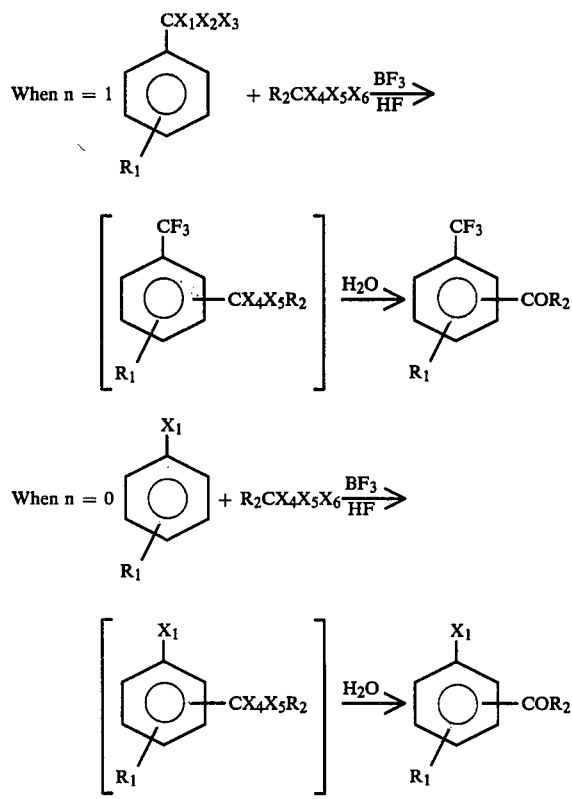

The $CCl_3$, $CBr_3$, $CI_3$, $CF_2Br$, $CCl_2F$, $CBr_2F$, etc., groups are converted into $CF_3$ during the reaction in an HF medium, while the Cl, Br and I substituents are not affected.

The position of the $COR_2$ group with respect to the $CF_3$, $X_1$ and $R_1$ groups is in conformity with the substitution rules well known to the organic chemist.

The phenyl ketones obtained according to the process of the invention are useful as intermediates in the synthesis of compounds having a pharmaceutical or phytosanitary (e.g., herbicidal) activity.

The following are examples of compounds that can be prepared by the process according to the invention: 4-fluoroacetophenone; 4-chloroacetophenone; 2-fluoro-5-methylbenzophenone; 3-fluoro-6-methylbenzophenone; 2,4-dichlorobenzophenone; 2,4'-dichlorobenzophenone; 4-chloro-4'-bromobenzophenone; 4-fluoro-4'-bromobenzophenone; 4,4'-difluorobenzophenone; 4-trifluoromethyl-4'-fluorobenzophenone; 4,4'-difluoro-3-methylbenzophenone; 4,4'-difluoro-3-methoxybenzophenone; 2-fluoro-2'-chloro-5-methylbenzophenone; 3-fluoro-2'-chloro-6-methylbenzophenone; 2-fluoro-4'-chloro-5-methylbenzophenone; 3-fluoro-4'-chloro-6-methylbenzophenone; 4-fluoro-4'-chloro-3-methylbenzophenone; 2-trifluoromethyl-2'-fluoro-5-methylbenzophenone; and 2-trifluoromethyl-3'-fluoro-6'-methylbenzophenone.

In order to disclose more clearly the nature of the present invention, the following drawings and examples illustrating specific embodiments of the invention are given. It should be understood, however, that this is done solely by way of example and is intended neither to delineate the scope of the invention nor limit the ambit of the appended claims.

EXAMPLE 1

Into a 250 ml stainless steel reactor equipped with a magnetic stirrer system, 100 ml of anhydrous HF, 42.7 g (0.2 mole) of p-fluorotrichloromethylbenzene, and 22 g (0.2 mole) of orthofluorotoluene were introduced at about 0° C. The reactor was closed, after which gaseous boron trifluoride was introduced until a constant pressure of 6 bars was achieved. The reaction was then allowed to proceed with stirring at ambient temperature for 3 hours. After reaction, the reactor was decompressed to atmospheric pressure, and the reaction mixture poured over 200 g of crushed ice. Following warming up to ambient temperature, the heterogeneous mixture was stirred for one to two hours, then extracted three times with 200 ml of methylene chloride. The organic phases were washed three times with 200 ml of water, once with 200 ml of an aqueous 3% potassium hydroxide solution, and twice with 200 ml of water. The organic phase was dried over magnesium sulfate and the solvent eliminated by distillation under reduced pressure. 35.3 g (yield: 61.5%) of raw 4,4'-difluoro-3-methylbenzophenone was recovered.

EXAMPLE 2

The reaction was carried out as in Example 1 with the following compounds and under the following conditions:

| | |
|---|---|
| Anhydrous hydrofluoric acid | 00 g |
| Trichloromethylbenzene | 1.6 g (0.1 mole) |
| Fluorobenzene | 6 g (0.1 mole) |
| Boron trifluoride | bars at 20° C. |
| Temperature | 0° C. |
| Duration | hours |

18.5 g (yield: 92.5% of raw 4-fluorobenzophenone was recovered.

EXAMPLE 3

The reaction was carried out as in Example 1 with the following compounds and under the following conditions:

| | |
|---|---|
| Anhydrous hydrofluoric acid | 00 g |
| p-chlorotrifluoromethylbenzene | 8 g (0.1 mole) |
| Chlorobenzene | 1.2 g (0.1 mole) |
| Boron trifluoride | bars at 20° C. |
| Temperature | 0° C. |
| Duration | 5 hours |

21 g (yield: 89.4%) of a mixture of raw 2,4'-dichloro- and 4,4'-dichlorobenzophenone was recovered.

EXAMPLE 4

The reaction was carried out as in Example 1 with the following compounds and under the following conditions:

| | |
|---|---|
| Anhydrous hydrofluoric acid | 100 g |
| p-chlorotrichloromethylbenzene | 23 g (0.1 mole) |
| Chlorobenzene | 11.2 g (0.1 mole) |
| Boron trifluoride | 9 bars at 20° C. |
| Temperature | 80° C. |
| Duration | 18 hours |

20.2 g (yield: 86%) of a mixture of raw 2,4'-dichloro- and 4,4'-dichlorobenzophenone was recovered.

EXAMPLE 5

The reaction was carried out as in Example 1 with the following compounds and under the following conditions:

| | |
|---|---|
| Anhydrous hydrofluoric acid | 100 g |
| p-fluorotrichloromethylbenzene | 21.4 g (0.1 mole) |
| Fluorobenzene | 9.6 g (0.1 mole) |
| Boron trifluoride | 10 bars at 20° C. |
| Temperature | 100° C. |
| Duration | 8 hours |

19.2 g (yield: 88%) of a mixture of raw 4,4'-difluoro- and 2,4'-difluorobenzophenone was recovered.

EXAMPLE 6

The reaction was carried out as in Example 1 with the following compounds and under the following conditions:

| | |
|---|---|
| Anhydrous hydrofluoric acid | 100 g |
| Trifluoromethylbenzene | 29.2 g (0.2 mole) |
| Bromobenzene | 31.4 g (0.2 mole) |
| Boron trifluoride | 10 bars at 20° C. |
| Temperature | 50° C. |
| Duration | 4 hours |

49 g (yield: 93.8%) of raw 4-bromobenzophenone was recovered.

EXAMPLE 7

The reaction was carried out as in Example 1 with the following compounds and under the following conditions:

| | |
|---|---|
| Anhydrous hydrofluoric acid | 100 g |
| Trifluoromethylbenzene | 14.6 g (0.1 mole) |
| o-dichlorobenzene | 22 g (0.15 mole) |
| Boron trifluoride | 10 bars at 20° C. |
| Temperature | 60° C. |
| Duration | 4 hours |

24.9 g (yield: 99.2%) of a mixture of raw 2,3-dichloro- and 3,4-dichlorobenzophenone was recovered.

EXAMPLE 8

The reaction was carried out as in Example 1 with the following compounds and under the following conditions:

| | |
|---|---|
| Anhydrous hydrofluoric acid | 100 g |
| Trifluoromethylbenzene | 29.2 g (0.2 mole) |
| Boron trifluoride | 10 bars at 20° C. |
| Temperature | 80° C. |
| Duration | 6 hours |

27 g (yield: 54%) of raw 3-trifluoromethylbenzophenone was recovered.

EXAMPLE 9

The reaction was carried out as in Example 1 with the following compounds and under the following conditions:

| | |
|---|---|
| Anhydrous hydrofluoric acid | 100 g |
| 1,1,1-trichloroethane | 27 g (0.2 mole) |
| Orthodichlorobenzene | 14.7 g (0.1 mole) |
| Boron trifluoride | 6 bars at 20° C. |
| Temperature | 80° C. |
| Duration | 24 hours |

8.2 g (yield: 43%) of a mixture of raw 2,3-dichloro- and 3,4-dichloroacetophenone was collected.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed.

I claim:

1. A process for the preparation of phenyl ketones having the formula:

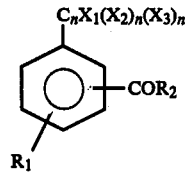

comprising the steps of:
(a) reacting a halobenzene or a trihalomethylbenzene having the formula:

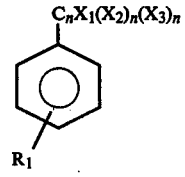 (I)

in a reaction vessel with a trihalomethylated aliphatic or aromatic compound having the formula:

$R_2CX_4X_5X_6$ (II)

in the presence of boron trifluoride in an amount such that the absolute pressure of boron trifluoride within the reaction vessel exceeds 1 bar and in the presence of hydrofluoric acid as a solvent; and
(b) hydrolyzing the resultant product;
wherein
n is 0 or 1;
$X_1$, $X_2$, and $X_3$ are Cl, Br, I, or F;

$R_1$ is at least one element or moiety selected from the group consisting of hydrogen, OH, Cl, Br, I, F, alkyl and alkoxy radicals having from 1 to 6 carbon atoms, and phenyl and phenoxy radicals substituted by at least one group more deactivating than $C_nX_1(X_2)_n(X_3)_n$;

$R_2$ is an aliphatic or aromatic radical; and $X_4$, $X_5$, and $X_6$ are Br, Cl, or F.

2. A process according to claim 1 wherein $R_2$ is alkyl, phenyl, alkylphenyl, phenylalkyl, or phenyl bearing at least one halogen, $NO_2$, CN, $NH_2$, or COOH substituent.

3. A process according to claim 1 wherein an amount of hydrofluoric acid is used such that the molar ratio of the hydrofluoric acid to the compound of Formula I is between 5 and 50.

4. A process according to claim 1 wherein the hydrofluoric acid used is anhydrous hydrofluoric acid.

5. A process according to claim 1 wherein the compounds of Formulas I and II are used in substantially equimolar amounts.

6. A process according to claim 1 wherein an amount of boron trifluoride is used such that the absolute pressure of boron trifluoride within the reaction vessel is between 6 and 20 bars.

7. A process according to claim 1 wherein step a is carried out at a temperature between $-20°$ C. and $150°$ C.

8. A process according to claim 1 wherein step b is carried out at a temperature between $0°$ C. and $80°$ C.

* * * * *